(12) United States Patent
Fukaya et al.

(10) Patent No.: US 12,174,210 B2
(45) Date of Patent: Dec. 24, 2024

(54) AUTOMATED ANALYZER AND CLEANING METHOD

(71) Applicant: Hitachi High-Tech Corporation, Tokyo (JP)

(72) Inventors: Masashi Fukaya, Tokyo (JP); Masaaki Hirano, Tokyo (JP); Akihiro Yasui, Tokyo (JP)

(73) Assignee: Hitachi High-Tech Corporation, Tokyo (JP)

( * ) Notice: Subject to any disclaimer, the term of this patent is extended or adjusted under 35 U.S.C. 154(b) by 900 days.

(21) Appl. No.: 17/276,966

(22) PCT Filed: Jul. 2, 2019

(86) PCT No.: PCT/JP2019/026299
§ 371 (c)(1),
(2) Date: Mar. 17, 2021

(87) PCT Pub. No.: WO2020/066198
PCT Pub. Date: Apr. 2, 2020

(65) Prior Publication Data
US 2022/0034927 A1 Feb. 3, 2022

(30) Foreign Application Priority Data
Sep. 27, 2018 (JP) .................. 2018-181564

(51) Int. Cl.
*G01N 35/10* (2006.01)
*C12M 1/36* (2006.01)
*F03G 7/00* (2006.01)

(52) U.S. Cl.
CPC ......... *G01N 35/1004* (2013.01); *C12M 41/48* (2013.01); *F03G 7/017* (2021.08); *B01D 2321/40* (2013.01); *C02F 2209/36* (2013.01)

(58) Field of Classification Search
CPC ....... G01N 35/1004; G01N 2035/1006; C12M 41/48; F03G 7/017; B01D 2321/40; C02F 2209/36
See application file for complete search history.

(56) References Cited

U.S. PATENT DOCUMENTS

2014/0377132 A1* 12/2014 Shimase ............ G01N 35/1004
422/67
2019/0049477 A1 2/2019 Muramatsu et al.

FOREIGN PATENT DOCUMENTS

| CN | 104903729 A | * | 9/2015 | ......... G01N 35/1002 |
| JP | 2011078881 A | * | 4/2011 | |
| WO | 2017145672 A1 | | 8/2017 | |

OTHER PUBLICATIONS

Search Report mailed Sep. 24, 2019 in International Application No. PCT/JP2019/026299.
(Continued)

*Primary Examiner* — Jill A Warden
*Assistant Examiner* — John McGuirk
(74) *Attorney, Agent, or Firm* — Miles & Stockbridge, P.C.

(57) ABSTRACT

In this invention, there are cleaning positions 25a, 25b, and 25c where cleaning tanks 19, 20, and 21 discharge cleaning water onto the surfaces of nozzles 10, 12, and 14 and drying positions 26a, 26b, and 26c where the cleaning water adhered to the surfaces of the nozzles 10, 12, and 14 is sucked up. During movement from the cleaning positions 25a, 25b, and 25c for the nozzles 10, 12, and 14 to the drying positions 26a, 26b, and 26c for the nozzles 10, 12, and 14, a control device 24 causes system water to be discharged from the nozzles 10, 12, and 14 for a first time, and during the sucking up of the cleaning water on the surfaces of the nozzles 10, 12, and 14 at the drying positions 26a, 26b, and 26c, the control device 24 causes the system water to be (Continued)

discharged from the nozzles 10, 12, and 14 for a second time. As a result, it is possible to effectively remove adhered water drops during nozzle cleaning.

8 Claims, 7 Drawing Sheets

(56) References Cited

OTHER PUBLICATIONS

Written Opinion mailed Sep. 24, 2019 in International Application No. PCT/JP2019/026299.

* cited by examiner

[FIG. 1]
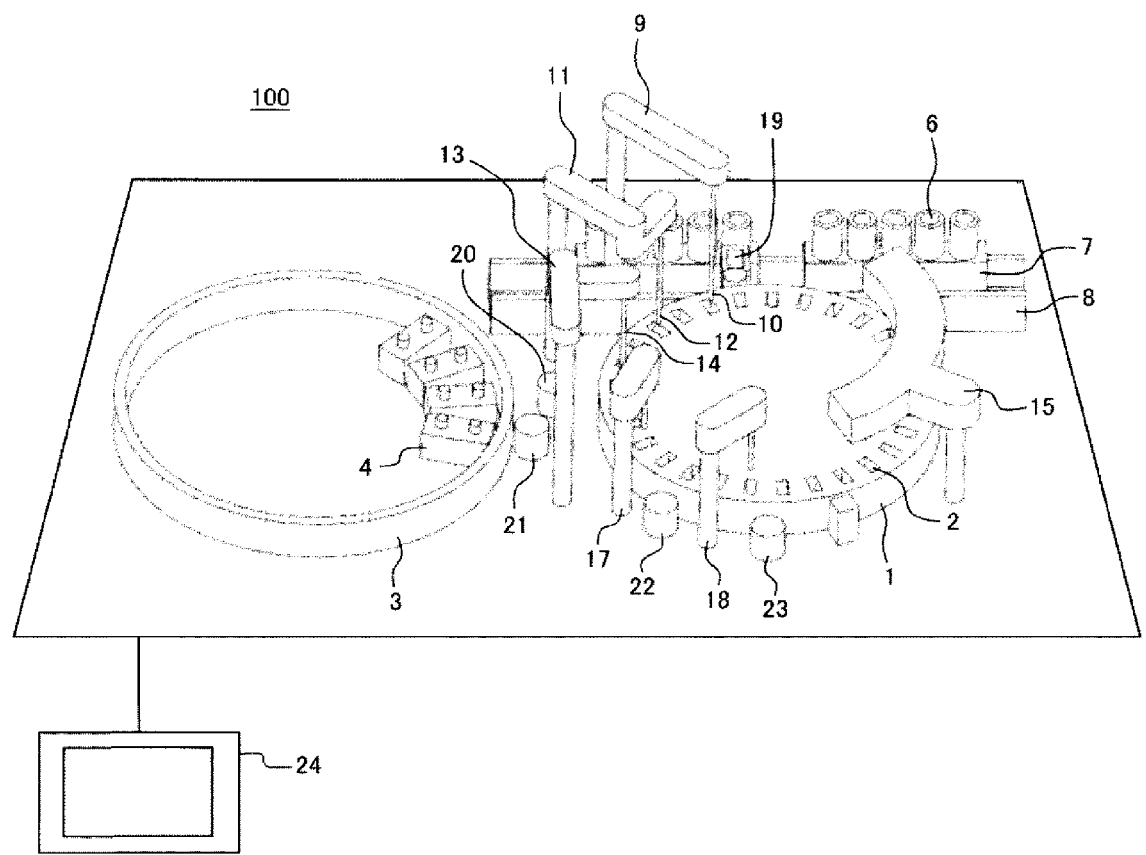

[FIG. 2]
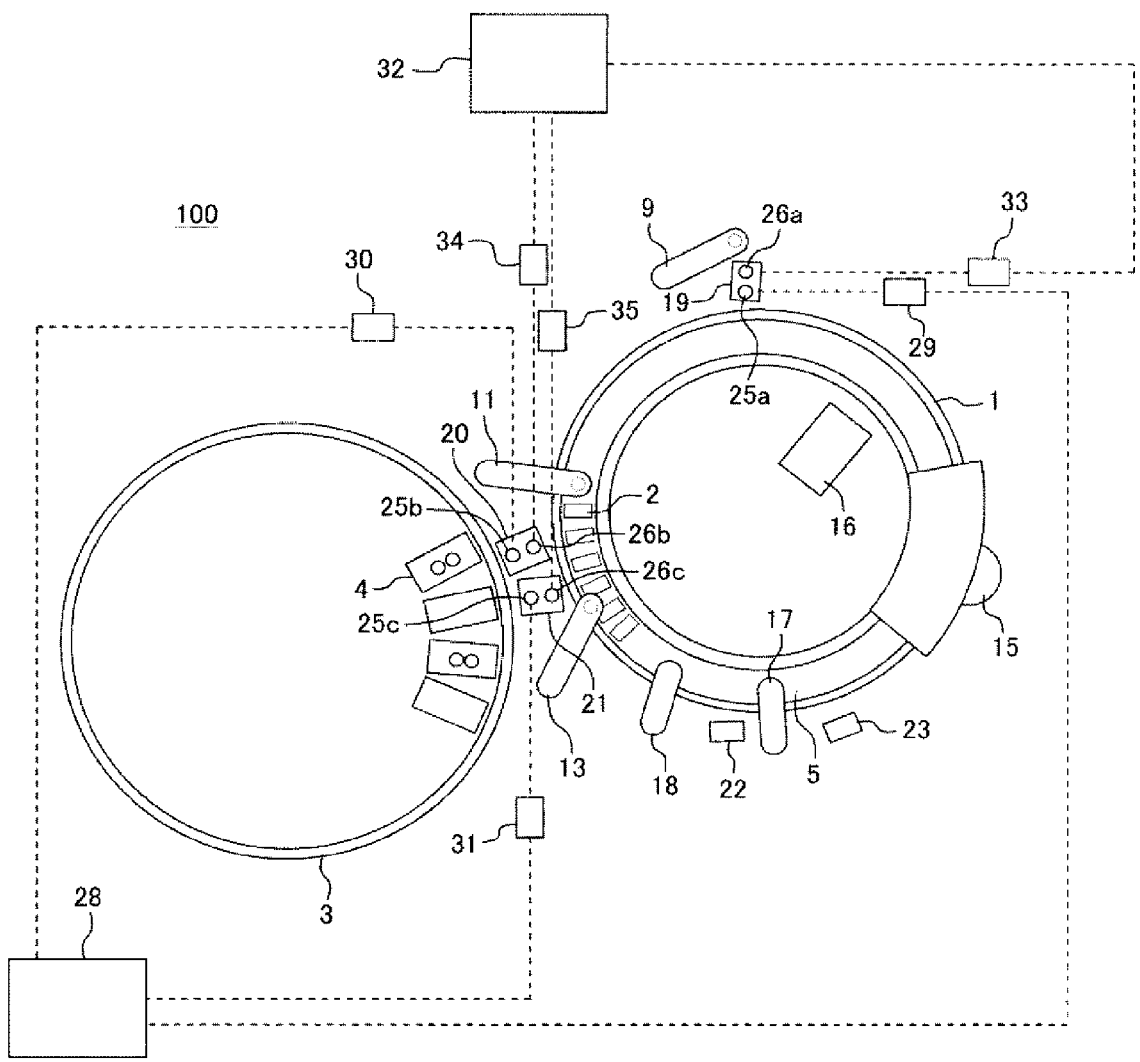

[FIG. 3]
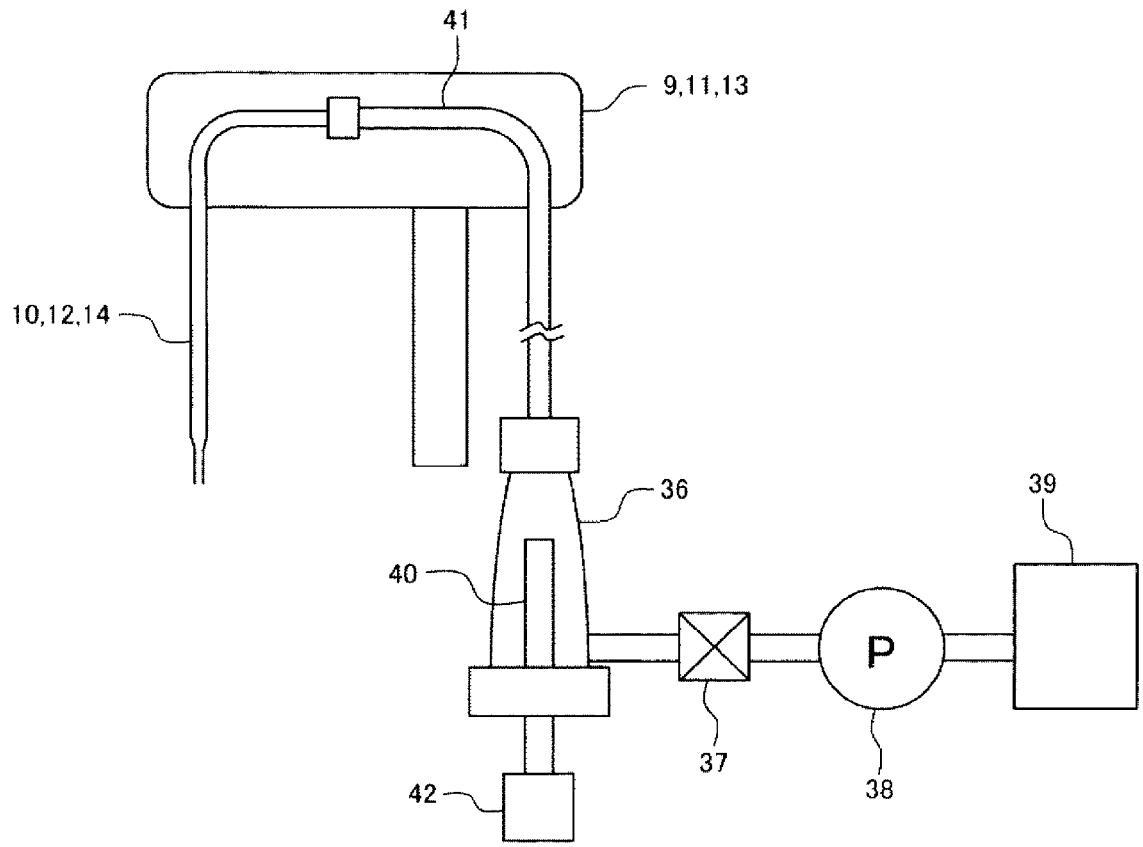
[FIG. 4]
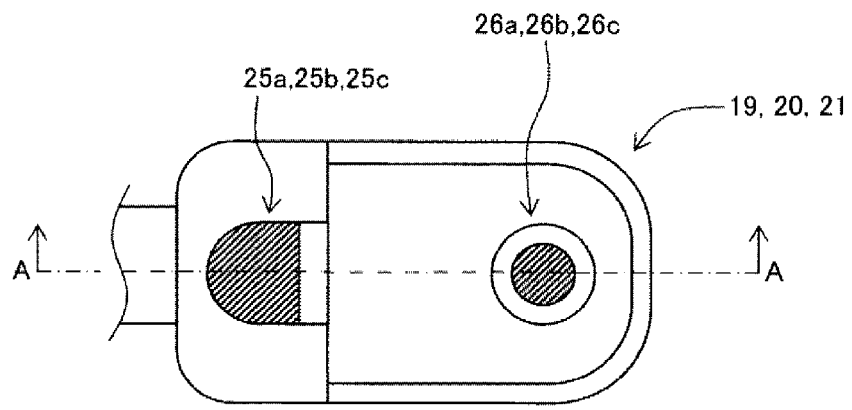

[FIG. 5]
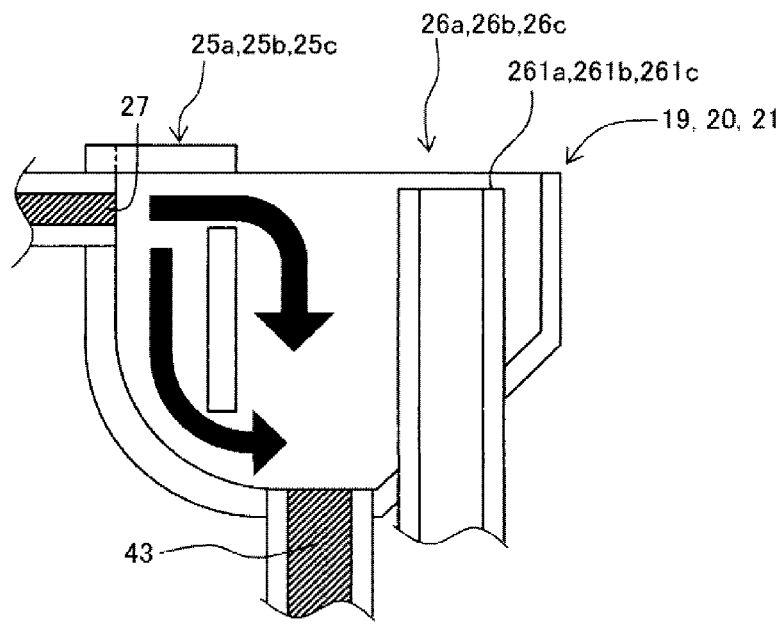
[FIG. 6]
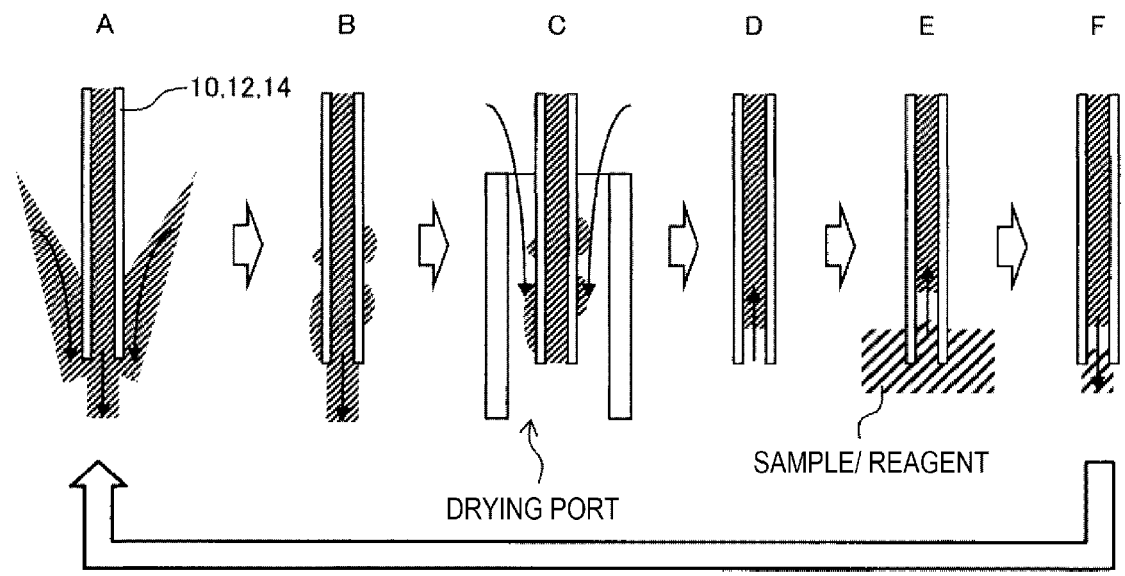

[FIG. 7]
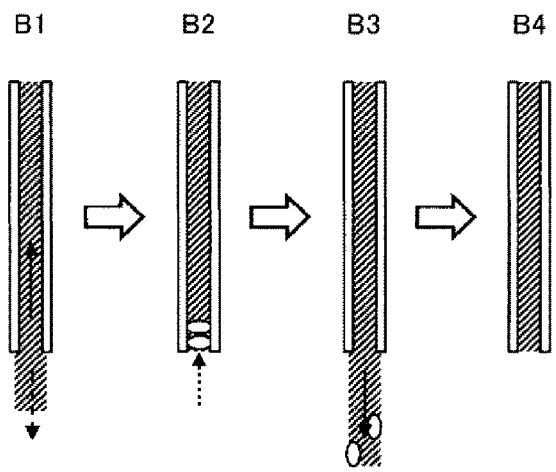
[FIG. 8]
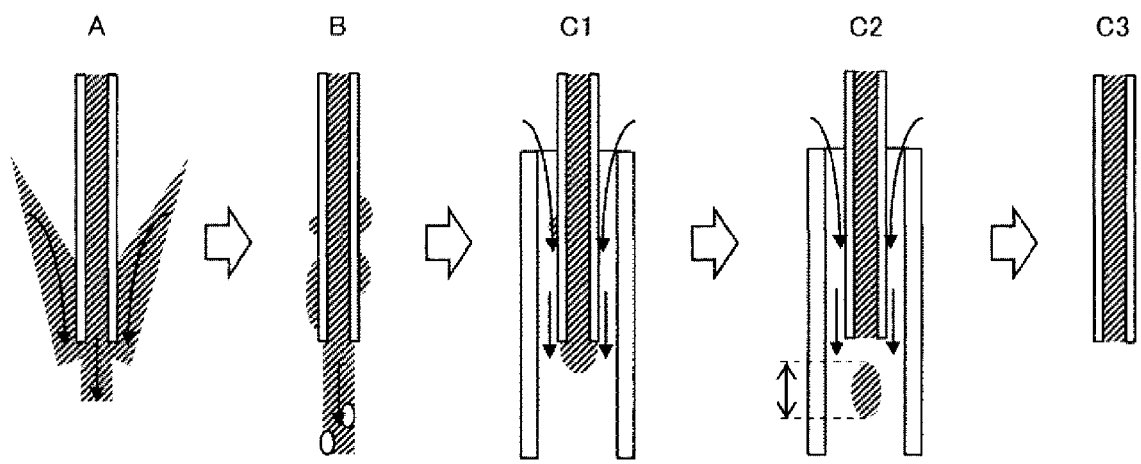

[FIG. 9]
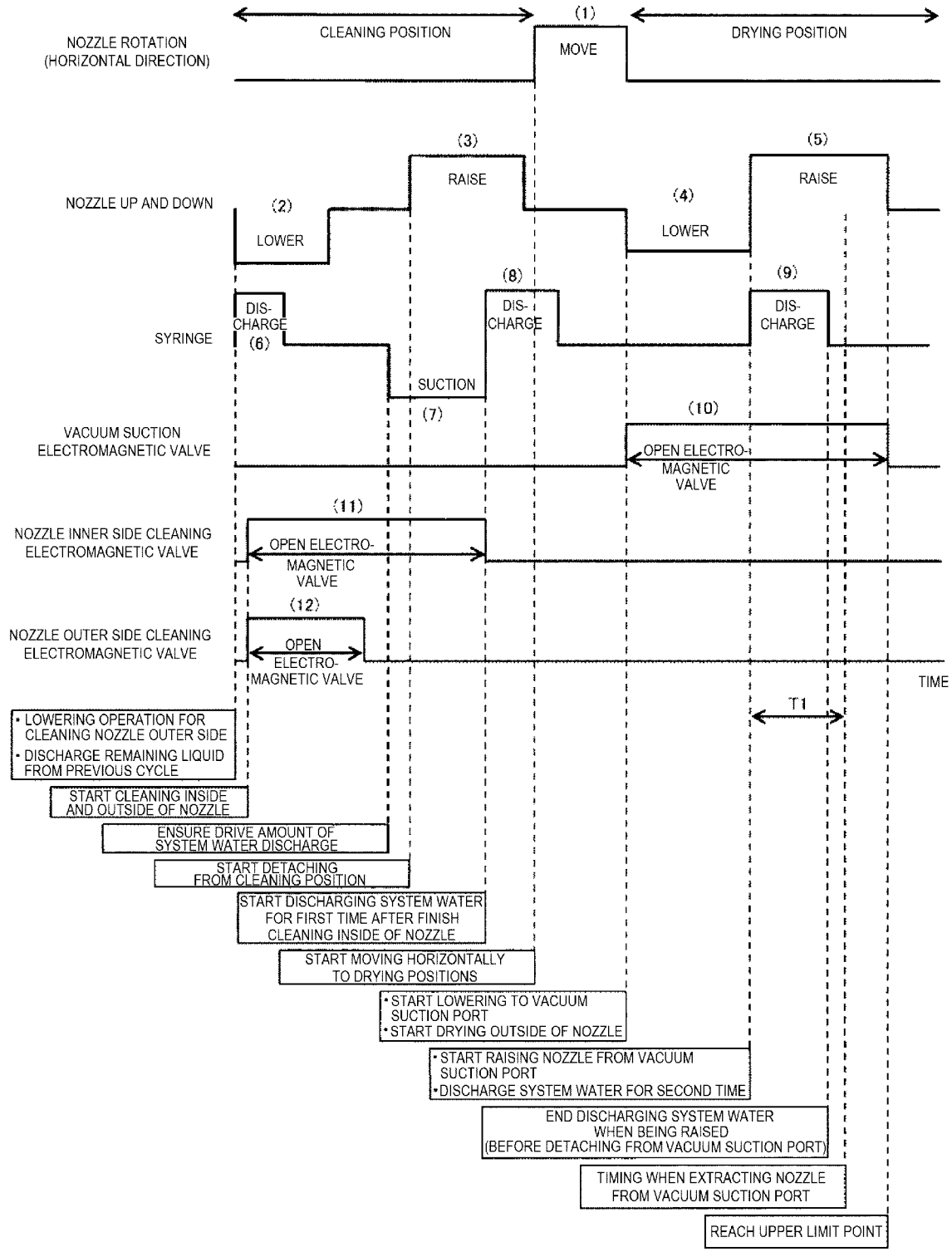

[FIG. 10]
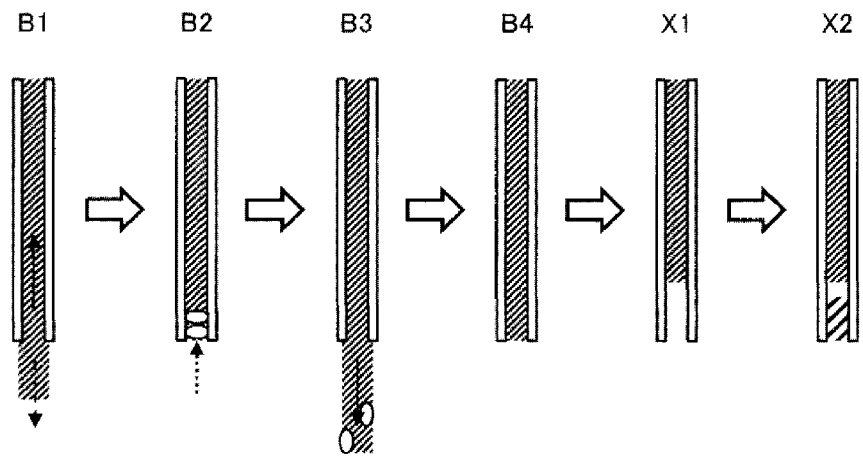
[FIG. 11]
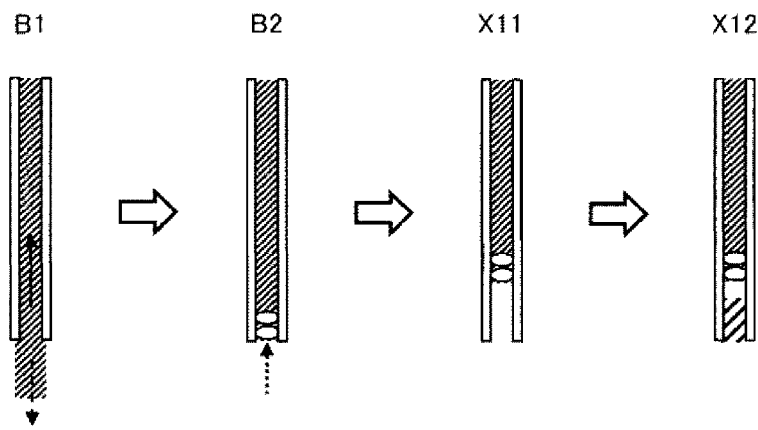
[FIG. 12]
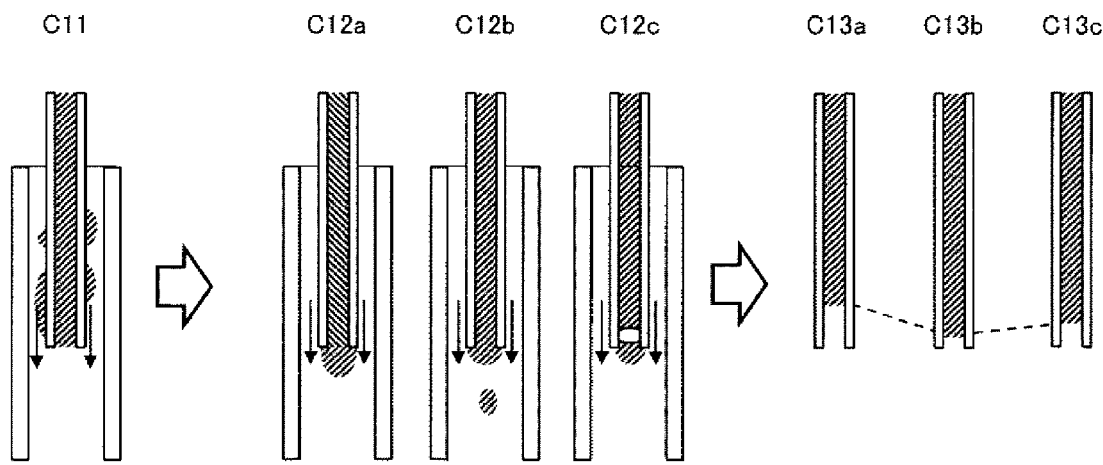

AUTOMATED ANALYZER AND CLEANING METHOD

TECHNICAL FIELD

The present invention relates to an automated analyzer and a cleaning method.

BACKGROUND ART

The automated analyzer is an apparatus that analyzes biological samples such as blood, urine and cerebrospinal fluid. In the automated analyzer, since a nozzle for dispensing samples and reagents handles various samples and reagents, cleaning must be performed for each dispensing operation in order to prevent carry-over of these components. The automated analyzer is provided with a cleaning tank for cleaning the nozzle. In a related-art automated analyzer, cleaning of an inner wall of a nozzle and cleaning of an outer wall of the nozzle are repeatedly performed for each dispensing operation in the cleaning tank.

On the other hand, cleaning water may remain as water droplets on an outer wall surface after nozzle cleaning. The water droplets cause a decrease in a concentration of the sample and the reagent in the vessel when the next sample and the reagent are dispensed. In recent years, in the automated analyzer, an influence of water droplets on measurement accuracy has become large due to a progress of improvement in dispensing accuracy and reduction in an amount of liquid to be dispensed, and the influence has become unignorable. In particular, in a reagent vessel or the like in which dispensing is performed a plurality of times from the same vessel, it is considered that the accumulation of the water droplets brought in largely appears as a decrease in a concentration component, and the measurement accuracy is lowered, since, for example, the dispensing operation is performed several hundred to several thousand times for a single vessel.

As a related-art technique for coping with such water droplets, for example, PTL 1 discloses an automated analyzer that measures a reaction liquid obtained by a chemical reaction in a reaction vessel and performs a component analysis, including: a nozzle configured to suction a sample or a reagent and discharge the sample or the reagent into a reaction vessel; a cleaning tank configured to clean the nozzle; a cleaning water supply unit configured to supply cleaning water for cleaning the nozzle to the cleaning tank; a compressed air supply unit configured to supply compressed air to the cleaning tank; and a controller configured to control the nozzle, the cleaning water supply unit, and the compressed air supply unit, in which the cleaning tank includes a cleaning water discharge port configured to discharge the cleaning water supplied from the cleaning water supply unit into the cleaning tank and a compressed air discharge port disposed on a trajectory of the cleaning water discharged from the cleaning water discharge port, and through which the compressed air supplied from the compressed air supply unit is discharged toward the nozzle inserted into the cleaning tank.

CITATION LIST

Patent Literature

PTL 1: WO-2017-145672

SUMMARY OF INVENTION

Technical Problem

However, in the case of removing water droplets from the nozzle by air blow as in the related art described above, it is difficult to control the flow of blown air, and there is a possibility of inducing scattering of the cleaning water. It is considered that since a region of the air to which the air blow is blown is limited, if a wide range of the nozzle is dried, there may be a case in which the remaining water droplets are not stable. As another drying method, in a case of using a method of drying the wide range of the nozzle by using decompression or vacuum suction, the flow of air is uniformly determined, scattering of water droplets can be prevented, and an effective range of a vacuum suction effect, that is, a drying range of the nozzle can also be controlled according to a shape of a suction port. However, it is considered that, when vacuum suction is used, water droplets adhering to a nozzle outer wall may be concentrated at a tip of the nozzle, and the water droplets may affect the next dispensing.

The present invention has been made in view of the above, and an object of the invention is to provide an automated analyzer and a cleaning method that can effectively remove adhering water droplets in cleaning of a nozzle.

Solution to Problem

In order to achieve the above object, the present invention provides an automated analyzer including a nozzle configured to dispense a dispensing target into a reaction vessel for causing a sample to be analyzed to react with a reagent; a measuring unit configured to measure a reaction liquid of the sample and the reagent in the reaction vessel; a cleaning tank configured to clean the nozzle; and a control device configured to control an operation of the nozzle, the measuring unit, and the cleaning tank, in which the cleaning tank includes a cleaning position configured to discharge cleaning water to a surface of the nozzle, and a drying position configured to suction the cleaning water adhering to the surface of the nozzle, the control device is configured to perform a first discharge of system water from the nozzle during a movement of the nozzle from the cleaning position to the drying position, and perform a second discharge of system water from the nozzle during a suction of the cleaning water on the surface of the nozzle at the drying position.

Advantageous Effect

According to the present invention, adhering water droplets in the cleaning of the nozzle can be effectively removed.

BRIEF DESCRIPTION OF DRAWINGS

FIG. 1 is a view schematically showing an overall configuration of an automated analyzer according to an embodiment of the invention.

FIG. 2 is a diagram schematically showing a flow path configuration of cleaning water and a piping configuration relating to vacuum suction extracted in the automated analyzer according to the embodiment of the invention.

FIG. 3 is a diagram schematically showing a configuration of a sample dispensing mechanism and a reagent dispensing mechanism.

FIG. 4 is a plan view schematically showing a configuration of a cleaning tank.

FIG. 5 is a sectional view taken along a line A-A in FIG. 4 schematically showing the configuration of the cleaning tank.

FIG. 6 is a diagram showing a flow of a series of a dispensing operation of a dispensing target by nozzles and cleaning processing.

FIG. 7 is a diagram showing details of a flow of a cleaning operation at a cleaning position of the cleaning tank.

FIG. 8 is a diagram showing details of a flow of a drying operation in a drying position of the cleaning tank.

FIG. 9 is a diagram showing a time chart of the cleaning processing.

FIG. 10 is a diagram showing an effect of the discharge (first time) of system water after the cleaning operation.

FIG. 11 is a diagram showing a comparative example in a case where the system water is not discharged after the cleaning operation.

FIG. 12 is a diagram showing a comparative example of the present embodiment in a case where the system water is not discharged in the drying operation.

DESCRIPTION OF EMBODIMENTS

Hereinafter, an embodiment of the present invention will be described with reference to FIGS. 1 to 9.

FIG. 1 is a diagram schematically showing an overall configuration of an automated analyzer according to the present embodiment. FIG. 2 is a diagram schematically showing a flow path configuration of cleaning water and a piping configuration relating to vacuum suction extracted in the automated analyzer.

In FIGS. 1 and 2, an automated analyzer 100 is an apparatus that dispenses a sample and a reagent into a reaction vessel 2 respectively to cause reaction and measures the liquid obtained by reaction, and schematically includes a sample transport mechanism 8, a reagent disk 3, a reaction disk 1, a sample dispensing mechanism 9, reagent dispensing mechanisms 11, 13, stirring mechanisms 17, 18, a spectrophotometer 16 (measurement unit), a cleaning mechanism 15, and a control device 24.

In the reaction disk 1, the reaction vessels 2 are arranged in a circumferential direction. The reaction vessel 2 is a vessel for accommodating a mixed liquid in which the sample and the reagent are mixed, and a plurality of reaction vessels 2 are arranged side by side on the reaction disk 1. The sample transport mechanism 8 that transports a sample rack 7 on which a plurality of sample vessels 6 each accommodating a sample to be analyzed are mounted is disposed near the reaction disk 1. The reaction vessel 2 is immersed in a reaction tank 5 filled with a thermally conductive medium (for example, constant temperature water) whose temperature is controlled at, for example, 37° C., and the constant temperature water circulates in the reaction tank 5, so that the temperature of the reaction vessel 2 is normally maintained at 37° C.

The reagent disk 3 is capable of placing a plurality of reagent bottles 4 containing reagents used for analysis on a circumference, has a role as a storage of the reagent bottles 4, and has a function of cooling the reagent bottles 4.

The sample dispensing mechanism 9 for dispensing the sample from the sample vessel 6 to the reaction vessel 2 are arranged, which is configured to be capable of rotationally moving and moving up and down between the reaction disk 1 and the sample transport mechanism 8, and a sample nozzle 10 disposed with a tip thereof facing downward is provided. In an operating range of the sample dispensing mechanism 9, a cleaning tank 19 for cleaning the sample nozzle 10 by the cleaning water is disposed. The reagent dispensing mechanisms 11, 13 for dispensing the reagent from the reagent bottles 4 to the reaction vessels 2 are provided, which are configured to be capable of rotationally moving in a horizontal direction and moving up and down between the reaction disk 1 and the reagent disk 3, and reagent nozzles 12, 14 are disposed respectively with tips thereof directed downward. In an operating range of the reagent dispensing mechanisms 11, 13, cleaning tanks 20, 21 for cleaning the reagent nozzles 12, 14 respectively by the cleaning water are disposed.

Around the reaction disk 1, the stirring mechanisms 17, 18, the spectrophotometer 16 that measures absorbance of a reaction liquid by measuring transmitted light obtained from a light source (not shown) via the reaction liquid in the reaction vessel 2, and the cleaning mechanism 15 that cleans the used reaction vessel 2 and the like are disposed.

The stirring mechanisms 17, 18 are configured to be capable of rotationally moving in the horizontal direction and moving up and down, and are inserted into the reaction vessels 2 to stir the mixed liquid (reaction liquid) of the sample and the reagent. In operating ranges of the stirring mechanisms 17, 18, cleaning tanks 22, 23 for cleaning the stirring mechanisms 17, 18 by cleaning water are disposed.

The control device 24 is configured with a computer or the like, controls an overall operation of the automated analyzer 100, and performs arithmetic processing for obtaining a concentration of a predetermined component in a liquid sample such as blood or urine. In FIG. 1, for the sake of simplicity, a connection relationship between the mechanisms that constitutes the automated analyzer 100 and the control device 24 is omitted.

FIG. 3 is a diagram schematically showing a configuration of the sample dispensing mechanism and the reagent dispensing mechanism.

As shown in FIG. 3, the sample dispensing mechanism 9 includes the sample nozzle 10 for suctioning a sample that is a dispensing target, and the reagent dispensing mechanisms 11, 13 include reagent nozzles 12, 14 for suctioning a reagent that is a dispensing target. In the following description, the sample nozzle 10 and the reagent nozzles 12, 14 are collectively referred to as nozzles 10, 12, and 14 unless when it is necessary to distinguish them from each other. The nozzles 10, 12, and 14 are joined to a tube 41 for drawing a flow path into the automated analyzer 100. The tube 41 constitutes a flow path that is connected to a water supply pump 39 via a syringe 36, an electromagnetic valve 37, and a liquid delivery pump 38 in this order from a joining side with the nozzles 10, 12, and 14. An inside of the series of flow paths (that is, an inside of the nozzles 10, 12, and 14 and the tube 41) is filled with water. Hereinafter, the water filling the inside of the flow paths is referred to as system water. A plunger 40 is disposed in the syringe 36. A motor 42 is connected to the plunger 40, and when the plunger 40 is driven by the motor 42, suction and discharge of the dispensing target (sample or reagent) in the nozzles 10, 12, and 14 are performed.

For example, when the sample is dispensed by the sample dispensing mechanism 9, the electromagnetic valve 37 is maintained in a closed state, and after the sample dispensing mechanism 9 is moved to a position (sample suction position) where the sample is suctioned from the sample vessel 6, the plunger 40 is driven in a suction direction in a state where a tip of the sample nozzle 10 reaches a liquid surface of the sample, and the sample is drawn into the sample nozzle 10. Thereafter, the sample dispensing mechanism 9 is moved to a position where the sample is discharged into the reaction vessel 2 (sample discharge position), and in this state, the plunger 40 is driven in a discharge direction to discharge the sample into the reaction vessel 2. After discharging the sample, the sample dispensing mechanism 9 moves to the cleaning tank 19 for cleaning the nozzle 10 to perform cleaning processing (described later).

Similarly, when the sample is dispensed by the reagent dispensing mechanisms 11, 13, the electromagnetic valve 37 is maintained in a closed state, and after the reagent dispensing mechanisms 11, 13 are moved to positions (sample suction positions) where the sample is suctioned from the reagent bottle 4, the plunger 40 is driven in the suction direction in a state where tips of the reagent nozzles 12, 14 reach a liquid surface of the reagent, and the reagent is drawn into the reagent nozzles 12, 14. Thereafter, the reagent dispensing mechanisms 11, 13 are moved to a position where the reagent is discharged into the reaction vessel 2 (reagent discharge position), and in this state, the plunger 40 is driven in the discharge direction to discharge the reagent into the reaction vessel 2. After discharging the reagent, the reagent dispensing mechanisms 11, 13 move to the cleaning tanks 20, for cleaning the nozzles 12, 14 to perform cleaning processing (described later).

FIGS. 4 and 5 are views schematically showing the configuration of the cleaning tank, FIG. 4 is an upper surface view, and FIG. 5 is a sectional view taken along a line A-A in FIG. 4.

In FIGS. 4 and 5, cleaning tanks 19, 20, and 21 include cleaning positions 25a, 25b, and 25c that discharge cleaning water to surfaces of nozzles 10, 12, and 14 and drying positions 26a, 26b, and 26c that suction the cleaning water adhering to the surfaces of the nozzles 10, 12, and 14, respectively.

A nozzle outer wall cleaning water discharge port 27 is disposed at an upper portion of the cleaning positions 25a, 25b, and 25c. As shown in FIG. 2, a water supply pump 28 is connected to the nozzle outer wall cleaning water discharge port 27, and the cleaning water supplied from the water supply pump 28 is discharged from the nozzle outer wall cleaning water discharge port 27. Electromagnetic valves 29, 30, and 31 are respectively disposed in the flow paths of the cleaning water from the water supply pump 28 to the nozzle outer wall cleaning water discharge port 27 of the cleaning tanks 19, 20, and 21, and presence or absence of the discharge of the cleaning water from the nozzle outer wall cleaning water discharge port 27 is controlled by controlling opening and closing of the electromagnetic valves 29, 30, and 31. At the cleaning positions 25a, 25b, and 25c, the cleaning water discharged from the nozzle outer wall cleaning water discharge port 27 is discharged from both an upper portion and a lower portion. Discharge ports 43 for discharging the cleaning water are respectively disposed below the cleaning tanks 19, 20, and 21, and the used cleaning water is discharged to an outside of the automated analyzer 100 through a waste liquid flow path (not shown) in the automated analyzer 100.

At the drying positions 26a, 26b, and 26c, cylindrical drying ports 261a, 261b, and 261c into which the nozzles 10, 12, and 14 can be inserted from above are formed. As shown in FIG. 2, a vacuum pump 32 is connected to the drying ports 261a, 261b, and 261c, and by transmitting reduced pressure of the vacuum pump 32 to the drying ports 261a, 261b, and 261c, the cleaning water is suctioned from the surfaces of the nozzles 10, 12, and 14 inserted into the drying ports 261a, 261b, and 261c. Electromagnetic valves 33, 34 and 35 are respectively disposed in tube paths from the vacuum pump 32 to the drying ports 261a, 261b, and 261c of the cleaning tanks 19, 20, and 21, and presence or absence of suction (vacuum suction) from the drying ports 261a, 261b, and 261c is controlled by controlling opening and closing of the electromagnetic valves 33, 34, and 35.

Inner diameters of the drying ports 261a, 261b, and 261c are formed to have appropriate sizes depending on outer diameters of the nozzles 10, 12, and 14 to be inserted. For example, the size of the inner diameter of each of the drying ports 261a, 261b, and 261c is set to be equal to or smaller than three times of the outer diameter of each of the nozzles 10, 12, and 14 in consideration of efficiency of suction of the cleaning liquid from an outer wall of each of the nozzles 10, 12, and 14. For example, when the outer diameter of each of the nozzles 10, 12, and 14 is 1.0 mm, the inner diameter of each of the drying ports 261a, 261b, and 261c is formed to be 3.0 mm or less.

In the analysis processing of the sample to be analyzed by the automated analyzer 100 configured as described above, first, the control device 24 dispenses a sample in the sample vessel 6 placed on the sample rack 7 transported to the vicinity of the reaction disk 1 by the sample transport mechanism 8 into the reaction vessel 2 on the reaction disk 1 by the sample nozzle 10 of the sample dispensing mechanism 9. After the dispensing, the sample nozzle 10 is cleaned in the cleaning tank 19. Next, the reagent used for the analysis is dispensed from the reagent bottle 4 on the reagent disk 3 to the reaction vessel 2 in which the sample is previously dispensed by the reagent nozzles 12, 14 of the reagent dispensing mechanisms 11, 13. After the dispensing, the reagent nozzles 12, 14 are cleaned in the cleaning tanks 20, 21. Subsequently, a mixed liquid of the sample and the reagent in the reaction vessel 2 is stirred by the stirring mechanisms 17, 18. Then, light generated by the light source is transmitted through the reaction vessel 2 containing the mixed liquid, and light intensity of the transmitted light is measured by the spectrophotometer 16. The light intensity measured by the spectrophotometer 16 is transmitted to the control device 24 via an A/D converter and an interface. Then, arithmetic processing is performed by the control device 24 to obtain a concentration of a predetermined component of the analysis item according to the reagent, and a result is displayed on a display unit (not shown) or stored in a storage unit (not shown). The light source (not shown), the spectrophotometer 16, and the control device 24 constitute a measurement unit that measures the reaction liquid of the sample and the reagent in the reaction vessel 2.

Here, the processing contents of the cleaning processing by the cleaning tanks 19, 20, and 21 of the sample nozzle 10 of the sample dispensing mechanism 9 and the reagent nozzles 12, 14 of the reagent dispensing mechanisms 11, 13 will be described.

FIG. 6 is a diagram showing a flow of a series of dispensing operations of a dispensing target by the nozzles and the cleaning processing, FIG. 7 is a diagram showing details of a flow of a cleaning operation at the cleaning position of the cleaning tank, and FIG. 8 is a diagram showing details of a flow of a drying operation at the drying position of the cleaning tank. FIG. 9 is a diagram showing a time chart of the cleaning processing.

As shown in FIG. 9, in the automated analyzer 100, the cleaning processing is performed before the dispensing operation. In the cleaning processing, the nozzles 10, 12, and 14 are inserted into the cleaning positions 25a, 25b, and 25c ((2) in FIG. 9). At this time, the plunger 40 of the syringe 36 is returned to a home position ((6) in FIG. 9). In the cleaning processing, the electromagnetic valve is opened ((11) and (12) in FIG. 9), and the cleaning of outsides of the nozzles and the cleaning of insides of the nozzles are performed (A in FIG. 6). The cleaning of the outsides of the nozzles 10, 12, and 14 is performed by discharging the cleaning water from the nozzle outer wall cleaning water discharge port 27. The cleaning of the insides of the nozzles 10, 12, and 14 is performed by pushing out the cleaning water from the water supply pump 39 and discharging the cleaning water from the tips of the nozzles 10, 12, and 14.

The cleaning of the outer walls and the cleaning of the inner walls of the nozzles 10, 12, and 14 do not necessarily need to be performed at the same timing as shown in FIG. 9, and are performed at timings suitable for preventing scattering of the cleaning water. A lowering amount of a cleaning range at the timings is set such that a sufficient range is cleaned with respect to a contamination range assumed for the nozzles 10, 12, and 14. For example, when it is assumed that the contamination range of the nozzles 10, 12, and 14 is 60 mm at the maximum from the tip, 65 mm from the tip is ensured as the cleaning range. In the case of a system in which the contamination range varies, the cleaning range may vary in accordance with the contamination range for each dispensing. However, in this case, a condition of the contamination range<the cleaning range is also maintained.

At the timings of the cleaning of the outer walls and the cleaning of the inner walls of the nozzles 10, 12, and 14, an operation of extracting the nozzles 10, 12, and 14 from the cleaning positions 25a, 25b, and 25c is performed ((3) in FIG. 9), and the plunger 40 of the syringe 36 is driven in the suction direction ((7) in FIG. 9). This is a preparatory operation for performing a system water discharge operation to be described later, and moves in the suction direction by a sufficient amount that can ensure a drive amount of system water discharge for twice. A movement amount of the plunger 40 at the time is, for example, a drive amount that allows only 100 μL system water to be discharged.

Subsequently, after the cleaning of the insides of the nozzles 10, 12, and 14, delivery of the cleaning water from the liquid delivery pump is stopped by the electromagnetic valve ((11) in FIG. 9).

Subsequently, the plunger 40 is driven to a discharge side ((8) in FIG. 9), and the system water is discharged (first time) from the nozzles 10, 12, and 14 (B in FIG. 6). At this time, the discharge of the system water is performed until a region where an air layer is mixed at each of the tips of the nozzles 10, 12, and 14 is discharged (B1 to B4 in FIG. 7). A discharge amount of the system water at this time is, for example, 80 μL. It is assumed that positions where the system water is discharged are the cleaning positions 25a, 25b, and 25c, or between the cleaning positions 25a, 25b, and 25c and the drying positions 26a, 26b, and 26c in the cleaning tanks 19, 20, and 21.

FIG. 10 is a diagram showing an effect of the discharge (first time) of the system water after the cleaning operation. FIG. 11 is a diagram showing a comparative example in a case in which the system water is not discharged after the cleaning operation.

As shown in FIGS. 10 and 11, after the cleaning of the insides of the nozzles 10, 12, and 14, air may be mixed into a region filled with the system water at the tips of the nozzles 10, 12, and 14 (B1 and B2 in FIGS. 10, and B1 and B2 in FIG. 11). If it is assumed that the processing proceeds to a next air suction step in a state in which the air is mixed, a plurality of air layers are generated in the nozzle (X11 in FIG. 11). If a reagent suctioning operation is performed in this state, the plurality of air layers become cushions against a pressure at the time of reagent suctioning and discharging, and variations occur in a reagent suction amount, a discharge amount, and a reagent component dilution rate (X12 in FIG. 11).

On the other hand, in the present embodiment, the system water is discharged from each of the nozzles 10, 12, and 14 to the region where the air layers are mixed (B3 in FIG. 10). Accordingly, the region where air layers are mixed at each of the tips of the nozzles 10, 12, and 14 is discharged (B4, X1, and X2 in FIG. 10). That is, in the present embodiment, by the first discharge of the system water, the variation in the suction amount of the reagent and the reagent component dilution rate can be prevented, and the dispensing accuracy can be maintained. In FIGS. 7, 10, and 11, the water droplets of the cleaning water remaining on the outer walls of the nozzles 10, 12, and 14 in a stage of discharging the system water shown in FIG. 5B are not shown.

Subsequently, the nozzles 10, 12, and 14 are moved to the drying positions 26a, 26b, and 26c of the cleaning tanks 19, 20, and 21 ((1) in FIG. 9). As shown in FIG. 9, in the present embodiment, although a case is shown in which the movement to the drying positions 26a, 26b, and 26c is performed while the system water is discharged (first time), for example, the system water may be discharged (first time) within a period of time from the rising to the moving. At the drying positions 26a, 26b, and 26c, the electromagnetic valves 33, 34, and 35 are controlled to be opened ((10) in FIG. 9), the nozzles 10, 12, and 14 are lowered into the drying ports 261a, 261b, and 261c ((4) in FIG. 9), and the drying operation by vacuum suction is performed (C in FIG. 6). An opening control of the electromagnetic valves 33, 34, and 35 for vacuum suction is performed in accordance with the timing of insertion of the nozzles 10, 12, and 14 into the drying ports 261a, 261b, and 261c.

The lowering amount of the nozzles 10, 12, and 14 to the drying ports 261a, 261b, and 261c is set such that the drying range is equal to or greater than the cleaning range. For example, when a cleaning range of 65 mm from the tips of the nozzles 10, 12, and 14 is ensured, a range of 70 mm from the tips of the nozzles 10, 12, and 14 is inserted into the drying ports 261a, 261b, and 261c. In the case of a system in which the cleaning range varies, the drying range may vary in accordance with the variation of the cleaning range. However, even in this case, a condition of the cleaning range<the drying range is also maintained. That is, in consideration of the cleaning range as well, the apparatus always maintains a condition of the contamination range<the cleaning range<the drying range.

In the drying operation (C in FIG. 6), when the nozzles 10, 12, and 14 reach the lowest point set as the drying range, the plunger 40 is driven in the discharge direction ((5) in FIG. 9), the system water is discharged (second time) from the nozzles 10, 12, and 14 (C1 in FIG. 8), the water droplets collected at the tips of the nozzles 10, 12, and 14 are removed together with the discharged system water (C2 in FIG. 8), the nozzles 10, 12, and 14 are raised ((9) in FIG. 9), and the nozzles 10, 12, and 14 are pulled out from the drying ports 261a, 261b, and 261c (C3 in FIG. 8).

When the nozzles 10, 12, and 14 are inserted into the drying ports 261a, 261b, and 261c in the drying operation, water droplets of the cleaning water adhering to the outsides are collected at the tips of the nozzles 10, 12, and 14. The timing at which the water droplets are collected is substantially when the tips of the nozzles 10, 12, and 14 are lowered to the lowest point set as the drying range. Accordingly, by driving the plunger 40 to the discharge side at this timing to discharge a small amount of the system water from the tips of the nozzles 10, 12, and 14, the water droplets collected at the tips of the nozzles 10, 12, and 14 are caught in the system water pushed out from the insides of the nozzles 10, 12, and 14 to the tips thereof, and are suctioned into the drying ports 261a, 261b, and 261c, and thus the water droplets can be stably removed, and tip states of the nozzles 10, 12, and 14 can be made uniform every time the cleaning processing is performed.

FIG. 12 is a diagram showing a comparative example of the present embodiment in a case where the system water is not discharged in the drying operation.

As shown in FIG. 12, during the drying operation, when the nozzles 10, 12, and 14 are inserted into the drying ports 261a, 261b, and 261c and the vacuum suction is performed, water droplets adhering to the outer walls of the nozzles 10, 12, and 14 may be collected at the tips of the nozzles 10, 12, and 14 (C11 in FIG. 12). If the system water is not discharged in the drying operation, the water droplets collected at the tips of the nozzles 10, 12, and 14 may be drawn into the drying ports 261a, 261b, and 261c, or may move to the next operation while adhering to the nozzles.

In addition, since an amount of water droplets collected at the tips of the nozzles 10, 12, and 14 depends on an amount of cleaning water adhering to the outer walls of the nozzles 10, 12, and 14 at the time of cleaning, the amount of water droplets varies every time the drying operation is performed depending on a condition of the nozzle surface. That is, a removal state of the water droplets collected at the tips of the nozzles 10, 12, and 14 in the drying operation also varies (C12a, C12b, and C12c in FIG. 12). Accordingly, when partition air is suctioned in a state in which there is variation in the removal state of the water droplets, variation occurs in the suction amount of the reagent and the reagent component dilution rate (C13a, C13b, and C13c in FIG. 12). The variation in the partition air amount affects response accuracy of the pressure change of the syringe 36 and the plunger 40, and thus causes the variation at the time of the reagent discharge.

On the other hand, in the present embodiment, in the drying operation, the system water is discharged (second time) from the nozzles 10, 12, and 14 inserted in the drying port 261a, 261b, and 261c (C1 in FIG. 8), and the water droplets collected at the tips of the nozzles 10, 12, and 14 are removed together with the discharged system water (C2 in FIG. 8). Accordingly, the variation in the suction amount of the reagent and the reagent component dilution rate can be prevented.

Subsequently, after the nozzles 10, 12, and 14 are raised from the drying ports 261a, 261b, and 261c, the nozzles 10, 12, and 14 are moved to the sample suction position and the reagent suction position. At the time, suction is performed by the syringe 36 and the plunger 40, and a layer of air (partition air) is taken into the tips of the nozzles 10, 12, and 14 (D in FIG. 6). Suction of the partition air (air suction) is performed even when the nozzles 10, 12, and 14 are in operation. The partition air has an effect of avoiding a contact with the system water at the time of suctioning the reagent. After the air suction, the sample dispensing mechanism 9 lowers the sample nozzle 10 to the sample vessel 6 to suction the sample (E in FIG. 6), and then moves the sample nozzle 10 to the reaction vessel 2 to discharge the sample (F in FIG. 6), and the dispensing operation ends. Similarly, after the air suction, the reagent dispensing mechanisms 11, 13 lower the reagent nozzles 12, 14 to the reagent bottle 4 to suction the reagent (E in FIG. 6), and then moves the reagent nozzles 12, 14 to the reaction vessel 2 to discharge the reagent (F in FIG. 6), and the dispensing operation ends. In this way, by repeating the operations of A to F in FIG. 6, the dispensing is repeatedly performed.

The discharge amount of the system water in the drying operation needs to be an amount by which the water droplets collected at the tips of the nozzles 10, 12, and 14 are sufficiently dropped at the time of suction at the drying ports 261a, 261b, and 261c while the flow of the water into the vacuum pump 32 is minimized. That is, the discharge amount of the system water in the drying operation needs to be within a discharge amount range that satisfies the conditions. Here, a method of determining a lower limit value and an upper limit value of an optimum range of the discharge amount of the system water in the drying operation will be described.

Since surface tension acts on the liquid, it is necessary to discharge a sufficient amount of liquid in consideration of a shape of the tip of each of the nozzles 10, 12, and 14. Here, a lower limit value V1 of the discharge amount of the system water from the nozzles 10, 12, and 14 in the drying ports 261a, 261b, and 261c in the drying operation is determined as follows. That is, for example, when the lower limit value V1 of the discharge amount of the system water in the drying operation is V1, and the outer diameters of the nozzles 10, 12, and 14 are R1, the lower limit value V1 is determined so as to satisfy the following (Equation 1).

$$V1 \geq (4\pi((R1/2)^3)/3) \times 10 \quad \text{(Equation 1)}$$

The above (Equation 1) shows that the discharge amount V1 is 10 times or more of the volume of a sphere when considering the sphere having the same diameter as the outer diameter R1 of the tips of the nozzles 10, 12, and 14. For example, when the outer diameter R1 of each of the nozzles 10, 12, and 14 is 0.8 mm, the discharge amount of the system water is set to 2.68 µL or more.

In another example, when the lower limit value of the discharge amount of the system water is V2, and the inner diameter of each of the nozzles 10, 12, and 14 is R2, the lower limit value V2 is determined so as to satisfy the following (Equation 2).

$$V2 \geq \pi((R2/2)^3) \times 10 \quad \text{(Equation 2)}$$

In the above (Equation 2), an amount of system water to be discharged is determined in consideration of the range of the air layer (see C12c in FIG. 12) taken into the nozzles 10, 12, and 14. For example, when the inner diameter of each of the nozzles 10, 12, and 14 is 0.6 mm, the discharge amount of the system water is set to 2.83 µL or more.

It is assumed that a driving speed of the plunger 40 when the system water is discharged (second time) at the drying ports 261a, 261b, and 261c is sufficiently low compared to the system water discharge (first time) after the cleaning operation and the discharge operation of the sample and the reagent to the reaction vessel 2 at the time of the operation. For example, a discharge speed at which the system water is discharged (second time) in the drying ports 261a, 261b, and 261c is set to 50% or less of the discharge speed at which the system water is discharged (first time). This is to minimize the influence of a phenomenon in which the system water is excessively discharged from the tips of the nozzles 10, 12, and 14 when the discharge operation is performed at high speed (hereinafter, referred to as excessive discharge).

Next, an upper limit value V3 of the discharge amount of the system water in the drying operation is determined as follows. That is, in a state in which the discharge amount of the system water in the drying ports 261a, 261b, and 261c is V3, the time during which the nozzles 10, 12, and 14 stay in the drying ports 261a, 261b, and 261c after the nozzles 10, 12, and 14 start to rise in a state in which the nozzles 10, 12, and 14 are lowered into the drying ports 261a, 261b, and 261c is T1 (ms: see FIG. 9), a discharge speed of the system water discharge (first time) is V1 (μL/ms) and the discharge speed of the system water discharge (second time) in the drying ports 261a, 261b, and 261c is V2, the upper limit value V3 is determined so as to satisfy the following (Equation 3) and (Equation 4).

$$V2 = 0.5 \times V1 \tag{Equation 3}$$

$$V3 = V2 \times T1 \tag{Equation 4}$$

That is, in the above (Equation 3) and (Equation 4), under the condition that the discharge speed V2 is 50% of the discharge speed V1, the amount that can be discharged at the discharge speed V2 during the time T1 is defined as the upper limit value V3 of the discharge amount of the system water discharge (second time) in the drying ports 261a, 261b, and 261c. The time T1 depends on the rising operation speed of the nozzles 10, 12, and 14 at the drying ports 261a, 261b, and 261c.

As described above, by setting the upper limit value V3 and the lower limit values V1, V2 of the discharge amount of the system water discharge (second time), a uniform nozzle tip state in each operation without collecting water droplets at the tips of the nozzles 10, 12, and 14 can be ensured. Further, a discharge speed of the system water discharge (second time) in the drying ports 261a, 261b, and 261c is set to be lower than the discharge speed of the system water discharge (first time), and the pushing out of the system water from the nozzles 10, 12, and 14 and the suction force of the drying ports 261a, 261b, and 261c are used together, and thus the water droplets at the tips of the nozzles 10, 12, and 14 are cut. Therefore, the influence of the variation due to the excessive discharge is reduced. Since the variation due to the excessive discharge of the tips of the nozzles 10, 12, and 14 can be reduced, the influence of the dilution of sample or reagent at the time of repeated dispensing due to the drying in the wide range of the nozzles 10, 12, and 14 can be prevented, and high accuracy of the dispensing accuracy even with respect to trace amount dispensing having high accuracy can be achieved.

The effects of the present embodiment configured as described above will be described.

In the related art of removing water droplets from the nozzle by air blow, it is difficult to control the flow of blown air, and there is a possibility of inducing scattering of the cleaning water. It is considered that, since a region of the air to which the air blow is blown is limited, if a wide range of the nozzle is dried, there may be a case where the remaining water droplets are not stable. As another drying method, in a case of using a method of drying the wide range of the nozzle by using decompression or vacuum suction, the flow of air is uniformly determined, scattering of water droplets can be prevented, and an effective range of a vacuum suction effect, that is, a drying range of the nozzle can also be controlled according to a shape of a suction port. However, it is considered that, when vacuum suction is used, water droplets adhering to a nozzle outer wall may be concentrated at a nozzle tip, and the water droplets may affect the next dispensing.

On the other hand, in the present embodiment, in the automated analyzer 100 that includes the nozzle that dispenses the dispensing target into the reaction vessel 2 for causing the sample to be analyzed to react with the reagent (for example, the sample nozzle 10, the reagent nozzles 12, 14); the measuring unit that measures the reaction liquid of the sample and the reagent in the reaction vessel 2 (for example, the light source, the spectrophotometer 16, and the control device 24); the cleaning tanks 19, 20 and 21 that clean the nozzles 10, 12 and 14; and the control device 24 that controls the operation of the nozzles 10, 12 and 14, the measuring unit (for example, the light source, the spectrophotometer 16, and the control device 24), and the cleaning tanks 19, 20, and 21, the cleaning tanks 19, 20, and 21 include cleaning positions 25a, 25b, and 25c that discharge cleaning water to surfaces of nozzles 10, 12, and 14 and drying positions 26a, 26b, and 26c that suction the cleaning water adhering to the surfaces of the nozzles 10, 12, and 14. The control device 24 performs the first discharge of the system water from the nozzles 10, 12, and 14 during the movement of the nozzles 10, 12, and 14 from the cleaning positions 25a, 25b, and 25c to the drying positions 26a, 26b, and 26c, and performs the second discharge of the system water from the nozzle during the suction of the cleaning water on the surfaces of the nozzles 10, 12, and 14 at the drying positions 26a, 26b, and 26c. Therefore, the adhering water droplets during the cleaning of the nozzles 10, 12, and 14 can be effectively removed.

APPENDIX

The invention is not limited to the above-described embodiment, and includes various modifications and combinations without departing from the scope thereof. The invention is not limited to a configuration including all the configurations described in the above embodiment, and includes a configuration in which a part of the configuration is deleted. Each of the above-mentioned configurations, functions, and the like may be partially or entirely implemented by designing using an integrated circuit. The above configurations, functions, or the like may be implemented by software by means of a processor interpreting and executing a program for implementing respective functions.

REFERENCE SIGN LIST 1 reaction disk
2 reaction vessel
3 reagent disk
4 reagent bottle
5 reaction tank
6 sample vessel
7 sample rack
8 sample transport mechanism
9 sample dispensing mechanism
10 sample nozzle
11, 13 reagent dispensing mechanism
12, 14 reagent nozzle
15 cleaning mechanism
16 spectrophotometer
17, 18 stirring mechanism
19 cleaning tank
20, 21 cleaning tank
22, 23 cleaning tank
24 control device
25a, 25b, 25c cleaning position
26a, 26b, 26c drying position
27 nozzle outer wall cleaning water discharge port
28 water supply pump
29, 30, 31 electromagnetic valve
32 vacuum pump
33, 34, 35 electromagnetic valve 36 syringe
37 electromagnetic valve
38 liquid delivery pump
39 water supply pump
40 plunger
41 tube
42 motor
43 discharge port
100 automated analyzer
261a, 261b, 261c drying port

The invention claimed is:

1. An automated analyzer comprising:
a nozzle that dispenses a dispensing target into a reaction vessel for causing a sample to be analyzed to react with a reagent;
a measuring unit that measures a reaction liquid of the sample and the reagent in the reaction vessel;
a cleaning tank that cleans the nozzle; and
a control device that controls an operation of the nozzle, the measuring unit, and the cleaning tank, wherein
the cleaning tank includes
a cleaning position comprising a nozzle outer wall cleaning water discharge port and a water supply pump that discharges cleaning water to an outer surface of the nozzle, and
a drying position comprising a drying port which is adapted to receive the nozzle when inserted from above and a vacuum pump that suctions the cleaning water adhering to the outer surface of the nozzle, and
the control device is configured to perform a first discharge of system water from the nozzle during a movement of the nozzle from the cleaning position to the drying position, and to perform a second discharge of system water from the nozzle during a suction of the cleaning water on the outer surface of the nozzle at the drying position.

2. The automated analyzer according to claim 1, wherein an inner diameter of the drying port is three times or less of an outer diameter of the nozzle.

3. The automated analyzer according to claim 1, wherein an amount of a system water discharged from the nozzle in the second discharge of system water at the drying position is smaller than an amount of a system water discharged from the nozzle in the first discharge of system water during the movement from the cleaning position to the drying position.

4. The automated analyzer according to claim 3, wherein a discharge speed of the system water discharged from the nozzle by the second discharge of system water at the drying position is 50% or less of a discharge speed of the system water discharged from the nozzle by the first discharge of system water during the movement from the cleaning position to the drying position.

5. The automated analyzer according to claim 3, wherein an upper limit value of the amount of system water discharged from the nozzle by the discharge of the second system water at the drying position under the control of the control device is determined by the control device based on a controlled staying time of the nozzle at the drying position and a controlled discharge speed of the system water from the nozzle.

6. The automated analyzer according to claim 3, wherein a lower limit value of the amount of system water discharged from the nozzle by the discharge of the second system water at the drying position under the control of the control device is determined by the control device based on an outer diameter of a tip of the nozzle.

7. The automated analyzer according to claim 3, wherein a lower limit value of the amount of system water discharged from the nozzle by the discharge of the second system water at the drying position under the control of the control device is determined by the control device based on an inner diameter of a tip of the nozzle.

8. A cleaning method of an automated analyzer, wherein the automated analyzer includes a nozzle that dispenses a dispensing target into a reaction vessel for causing a sample to be analyzed to react with a reagent; a measuring unit that measures a reaction liquid of the sample and the reagent in the reaction vessel; a cleaning tank that cleans the nozzle; and a control device that controls an operation of the nozzle, the measuring unit, and the cleaning tank, and the cleaning tank includes a cleaning position comprising a nozzle outer wall cleaning water discharge port and a water supply pump that discharges cleaning water to an outer surface of the nozzle, and a drying position comprising a drying port which is adapted to receive the nozzle when inserted from above and a vacuum pump that suctions the cleaning water adhering to the outer surface of the nozzle, the cleaning method of the automated analyzer comprising:
a step of performing a first discharge of system water from the nozzle during a movement of the nozzle from the cleaning position to the drying position; and
a step of performing a second discharge of system water from the nozzle during a suction of the cleaning water on the outer surface of the nozzle at the drying position.

* * * * *